(12) United States Patent
Mamula

(10) Patent No.: US 7,625,567 B1
(45) Date of Patent: Dec. 1, 2009

(54) INDUCTION OF IMMUNE RESPONSES TO ISOASPARTYL-MODIFIED ANTIGENS

(75) Inventor: Mark J. Mamula, Madison, CT (US)

(73) Assignee: Yale University, New Haven, CT (US)

( * ) Notice: Subject to any disclaimer, the term of this patent is extended or adjusted under 35 U.S.C. 154(b) by 1044 days.

(21) Appl. No.: 10/613,272

(22) Filed: Jul. 3, 2003

Related U.S. Application Data

(63) Continuation-in-part of application No. PCT/US02/00336, filed on Jan. 4, 2002.

(60) Provisional application No. 60/259,765, filed on Jan. 4, 2001.

(51) Int. Cl.
*A61K 39/00* (2006.01)
*A61K 39/02* (2006.01)
*A61K 39/12* (2006.01)
*C08H 1/00* (2006.01)

(52) U.S. Cl. .............. 424/204.1; 424/234.1; 424/277.1; 530/402; 530/403

(58) Field of Classification Search ........................ None
See application file for complete search history.

(56) References Cited

U.S. PATENT DOCUMENTS

| | | | | |
|---|---|---|---|---|
| 5,169,862 A | * | 12/1992 | Burke et al. | ................. 514/450 |
| 5,298,490 A | * | 3/1994 | Heavner et al. | ................. 514/17 |
| 5,565,202 A | * | 10/1996 | Witter | ..................... 424/202.1 |
| 5,582,831 A | | 12/1996 | Shinitzki | |
| 5,733,540 A | | 3/1998 | Lee | |
| 5,872,104 A | | 2/1999 | Vermeulen et al. | |
| 5,965,381 A | | 10/1999 | Bruggen et al. | |
| 6,812,023 B1 | * | 11/2004 | Lamparski et al. | .......... 435/325 |

FOREIGN PATENT DOCUMENTS

WO WO 97/33612 9/1997
WO WO97/34613 * 9/1997

OTHER PUBLICATIONS

Bodey et al, (Anticancer Research, 2000, vol. 20, pp. 2665-2676).*
Schultze et al (Trends in Immunology, 2004, vol. 25, pp. 659-664).*
Addissson et al (PNAS, vol. 92, pp. 8522-8526).*
Le Fur et al (PNAS, 1997, vol. 94, pp. 7561-7565).*
Abstract of Wheeler (Salud p'ublica de M'exico, (Jul.-Aug. 1997) 39 (4) 283-7).*
Efferson et al (Anticancer research, 2005, vol. 25, pp. 715-724.*
Bachman et al (Journal of Immunology, 2005, vol. 175, pp. 4677-4685).*
Ramakrishna and Shinitzky (Cancer Immunol Immunother, 1991, vol. 33, pp. 1-8).*
Desrivieres et al (JBC, 1997, vol. 272, pp. 2470-2476).*
Azorsa et al (Blood, 1991, vol. 78, pp. 280-284).*
Mamula, Immunological Rev, 1998, vol. 164, pp. 231-239.*
Mamula et al, J Biol Chem, 1999, vol. 274, pp. 22321-22327.*
Aswad et al (Journal of Pharmaceutical and Biomedical Analysis, 2000, vol. 21, pp. 1129-1136).*
Nossal, Annual Review in Immunology, 1983, vol. 1, pp. 33-62.*
Sabin et al, JAMA, 1984, vol. 251, pp. 2988-2993.*
Lycke et al, Sandinavian Journal of Immunology, 1987, vol. 25, pp. 407-412.*
Smith et al (Immunology, 2002, vol. 106, pp. 144-158).*
Mamula et al (Journal of Biological Chemistry, 1999, vol. 274, pp. 22321-22327).*
The abstract of Disis et al (Critical Reviews in Immunology, 1998, vol. 18, pp. 37-45).*
Gene Bank Accession No. BAA32580, Nov. 9, 2007.*
Ryttersgaard, C., et al., "Crystal Structure of Human L-Isoaspartyl Methyltransferase," *J. Biol. Chem.* 277:10642-10646. (Mar. 22, 2002), The American Society for Biochemistry and Molecular Biology, Inc. (published online Jan. 2002).

* cited by examiner

*Primary Examiner*—Karen A Canella
(74) *Attorney, Agent, or Firm*—Todd E. Garabedian; Wiggin and Dana LLP

(57) ABSTRACT

The present invention is directed to a method of enhancing the immune response of a patient relative to the normal immune response, by administering isoaspartyl-modified proteins, peptides, or cells, to a patient. The present invention is also directed to vaccines containing the isoaspartyl-modified proteins, peptides, or cells, as well as antibodies reactive with the isoaspartyl-modified proteins, peptides, or cells.

10 Claims, 9 Drawing Sheets

TRP-2 181-188 peptide sequence:

Peptide #1 : VYD (aspartyl) FFVWL

Peptide #2 : VYD (isoaspartyl) FFVWL

```
                        SEQUENCE LISTING

<160> NUMBER OF SEQ ID NOS: 4

<210> SEQ ID NO 1
<211> LENGTH: 9
<212> TYPE: PRT
<213> ORGANISM: Human

<400> SEQUENCE: 1

Tyr Met Asp Gly Thr Met Ser Gln Val
1               5

<210> SEQ ID NO 2
<211> LENGTH: 8
<212> TYPE: PRT
<213> ORGANISM: Human

<400> SEQUENCE: 2

Val Tyr Asp Phe Phe Val Trp Leu
1               5

<210> SEQ ID NO 3
<211> LENGTH: 8
<212> TYPE: PRT
<213> ORGANISM: Human
<220> FEATURE:
<223> OTHER INFORMATION: Xaa = Isoaspartyl at Position 3 (Residue 183)

<400> SEQUENCE: 3

Val Tyr Xaa Phe Phe Val Trp Leu
1               5

<210> SEQ ID NO 4
<211> LENGTH: 8
<212> TYPE: PRT
<213> ORGANISM: Human

<400> SEQUENCE: 4

Ser Ile Ile Asn Phe Glu Lys Leu
1               5
```

INDUCTION OF IMMUNE RESPONSES TO ISOASPARTYL-MODIFIED ANTIGENS

CROSS-REFERENCE TO RELATED APPLICATIONS

This application is a Continuation-in-Part of International Application No. PCT/US02/00336, filed Jan. 4, 2002, which claims the benefit of U.S. Provisional Application No. 60/259,765 filed Jan. 4, 2001. These applications are herein incorporated by reference in their entireties.

STATEMENT OF GOVERNMENT SUPPORT

This application was made with United States Government support under Award Numbers AI36529; 5RO1 AI-48120-03; 1R41DK-064528-01; and 1R41CA101542-01, all from the National Institutes of Health. The U.S. Government has certain rights in this invention.

BACKGROUND OF THE INVENTION

1. Field of the Invention

This invention relates to methods of treating tumors and bacterial or viral pathogens, and more particularly to methods of treating tumors and bacterial or viral pathogens using isoaspartyl-modified proteins to enhance immune response. The invention also relates to vaccines and antibodies used in these treatments.

2. Brief Description of the Related Art

The immune system has evolved to be tolerant of self-proteins by the deletion of autoreactive cells in the thymus or bone marrow and by the establishment of B and T lymphocyte anergy in the peripheral circulation (Billingham, R. E. et al., Nature 172:603-606, 1956; Schlid, H. et al., Science 247:587-589, 1990). These mechanisms are based on the presentation of a vast array of self-peptides to the lymphoid repertoire. Despite the efforts to instruct the immune system to ignore self-tissues, the appearance of various autoimmune diseases demonstrates that tolerance to self-antigens is not perfect. Flaws in the development of immune tolerance can be revealed by the immunization of animal models with a variety of self-peptides leading to B and T cell autoimmunity as well as autoimmune-mediated pathology (Lehman, P. V. et al., Nature 358:155-157, 1992; Mamula, M. J., J. Exp. Med. 177:567-571, 1993; Bockenstedt, L. K., et al., J. Immunol. 154:3516-3524, 1995).

How tolerance is broken in the initiation of autoimmunity is not completely understood. The immunization of mice with a single self-peptide, the amino-terminal 11 amino acids of myelin basic protein (MBP) in complete Freund's adjuvant can elicit pathology resembling that of human multiple sclerosis (Lehman, P. V. et al., Nature 358:155-157, 1992). The induction of disease requires a post-translationally acetylated form of MBP peptide 1-11. While this disease can be elicited with a single self-peptide or event with T cells of a single specificity, the autoimmune response diversifies to many sites on the MBP over the course of the disease. T cell responses originate with the dominant single self peptide but rapidly evolve to include other cryptic peptide epitopes within MBP. Similar observations of determinant spreading have been made in murine models of diabetes and systemic lupus erythematosus (SLE), two diseases arising spontaneously in susceptible strains of mice (Kaufman, D. L. et al., Nature 366:69-72, 1993; Bockenstedt, L. K., et al., J. Immunol. 154:3516-3524, 1995; Fatenejad, S. et al., J. Immunol. 152: 5523-5531, 1994).

Antinuclear antibodies specific for double-stranded DNA and the U1/Sm ribonucleoprotein particle (snRNP) are diagnostic markers of SLE. The snRNP particle is an RNA-protein complex essential for the splicing of pre-mRNA (Wassarman, D. A. et al., Science 257:1918-1925, 1992). Proteins designated B, B', and D comprise the target proteins of anti-Sm autoantibodies in SLE patients. It is not known how high affinity autoantibodies and autoreactive T cells arise to these intracellular proteins the mature phenotype of autoantibodies found in diseases such as SLE indicates that autoimmunity is driven by helper T lymphocytes and a source of antigen (Steinberg, A. D., et al., J. Immunol. 125:871-873, 1980; Jevnikar, A. M. et al., J. Exp. Med. 179:1137-1143, 1988; Tan, E. M. Adv. Immunol. 44:93-151, 1989).

While it is clear that autoimmunity can spread to several sites on an autoantigens over the course of experimentally induced disease models, the initiating antigenic peptide in naturally arising disease is unknown. A hypothesis of molecular mimicry implies that foreign pathogens that share amino acid sequences with self-peptides can break immunologic tolerance in the induction of autoimmunity. However, no pathogen has been unambiguously linked with the induction of any human autoimmune syndrome. Alternatively, the present inventors have initiated studies to consider forms of self-antigens that can be viewed as foreign by the immune system. The immune system does not respond to immunization with selected peptides from self-proteins. However, when the same self-peptides are converted to the isoaspartyl isoform, vigorous autoimmune responses develop upon immunization. After initiation by the isoaspartyl peptide isoforms, autoimmunity is amplified to other peptides on the autoantigen.

Isoaspartyl peptides arise spontaneously under physiologic conditions and are particularly elevated in cells undergoing stress and in aging cells. The presence of isoaspartyl peptides have been observed as a major component of the amyloid-containing brain plaques of patients with Alzheimer's disease. With relevance to immune responses, it is possible that tolerance to these forms of self proteins fails to occur early in lymphocyte development. Based on the enhanced immunity to some isoaspartyl self-peptides, it is possible that an accumulation of these aberrant peptides may be an early stimulus for autoimmune responses.

The present inventors have previously shown that isoaspartyl modifications of "self" proteins (e.g., proteins recognized by a cell as it's own) can result in autoimmunity. In these studies, it was shown that autoimmunity could be generated to isoaspartyl-modified self proteins, such as cytochrome c, while the identical unmodified protein would elicit no response from the immune system (Mamula, M. J. et al., J. Biol. Chem. 274:22321-22327, 1999). Applications of this phenomenon, however, were not disclosed.

Tumor antigens are considered a form of self protein to which little immune responses are generally elicited. This lack of immunity allows the tumor cells to proliferate and spread without the interference of immune responses that may attack and destroy the tumor cell. In a similar manner, many proteins on the surfaces of viral particles (such as gp proteins on the surface of HIV) are only weakly antigenic in eliciting responses of the immune system. These properties of viral and bacterial proteins allow for their survival in the host.

What is needed in the art is a method of identifying the weakly antigenic proteins found on tumors, bacteria and viruses, and a vaccine and antibody that can select and eliminate these weakly antigenic species. The present invention is believed to be an answer to that need.

SUMMARY OF THE INVENTION

In one aspect, the present invention is directed to a method of enhancing the immune response of a patient relative to the normal immune response, comprising the steps of: growing cells containing a tumor antigen, a bacterial protein, or a viral protein under conditions wherein an aspartic acid residue or an asparigine residue in the tumor antigen, the bacterial protein, or the viral protein is converted to an isoaspartic acid residue to produce an isoaspartic acid-containing tumor antigen, an isoaspartic acid-containing bacterial protein, or an isoaspartic acid-containing viral protein; optionally isolating the isoaspartic acid-containing tumor antigen, an isoaspartic acid-containing bacterial protein, or an isoaspartic acid-containing viral protein; and administering the cells or the isolated isoaspartic acid-containing tumor antigen, an isoaspartic acid-containing bacterial protein, or an isoaspartic acid-containing viral protein to the patient to enhance the immune response of the patient.

In another aspect, the present invention is directed to a method of enhancing the immune response of a patient relative to the normal immune response, comprising the steps of: administering to the patient a peptide comprising 9-40 amino acid residues of a tumor antigen, a bacterial protein, or a viral protein, wherein the peptide comprises an aspartic acid residue or an asparigine residue that has been replaced with an isoaspartic acid residue, to enhance the immune response of the patient.

In another aspect, the present invention is directed to a method of enhancing the immune response of a patient relative to the normal immune response, comprising the steps of: providing a tumor antigen, a bacterial protein, or a viral protein, or a fragment thereof, wherein each of the tumor antigen, bacterial protein, or viral protein, or fragment thereof, comprises an aspartic acid residue or an asparigine residue; treating the tumor antigen, bacterial protein, or viral protein, or fragment thereof, to convert the aspartic acid residue or the asparigine residue to an isoaspartic acid residue to produce an isoaspartic acid-containing tumor antigen, an isoaspartic acid-containing bacterial protein, or an isoaspartic acid-containing viral protein, or fragments thereof; and administering the isoaspartic acid-containing tumor antigen, the isoaspartic acid-containing bacterial protein, or the isoaspartic acid-containing viral protein, or fragments thereof, to the patient to elicit the enhanced immune response.

In another aspect, the present invention is directed to a vaccine, comprising a protein or fragment thereof, the protein selected from the group consisting of tumor antigens, bacterial proteins, viral proteins, and combinations thereof, the protein or fragment thereof comprising an isoaspartic acid residue; and a pharmaceutically acceptable carrier.

In another aspect, the present invention is directed to an antibody reactive with a protein or fragment thereof, the protein or fragment thereof comprising an isoaspartic acid residue, the protein or fragment thereof selected from the group consisting of tumor antigens, bacterial proteins, viral proteins, and combinations thereof.

These and other aspects will become apparent upon reading the following detailed description of the invention.

BRIEF DESCRIPTION OF THE DRAWINGS

The invention will be more fully understood from the following detailed description taken in conjunction with the accompanying drawings in which.

DETAILED DESCRIPTION OF THE INVENTION

Figure 1:
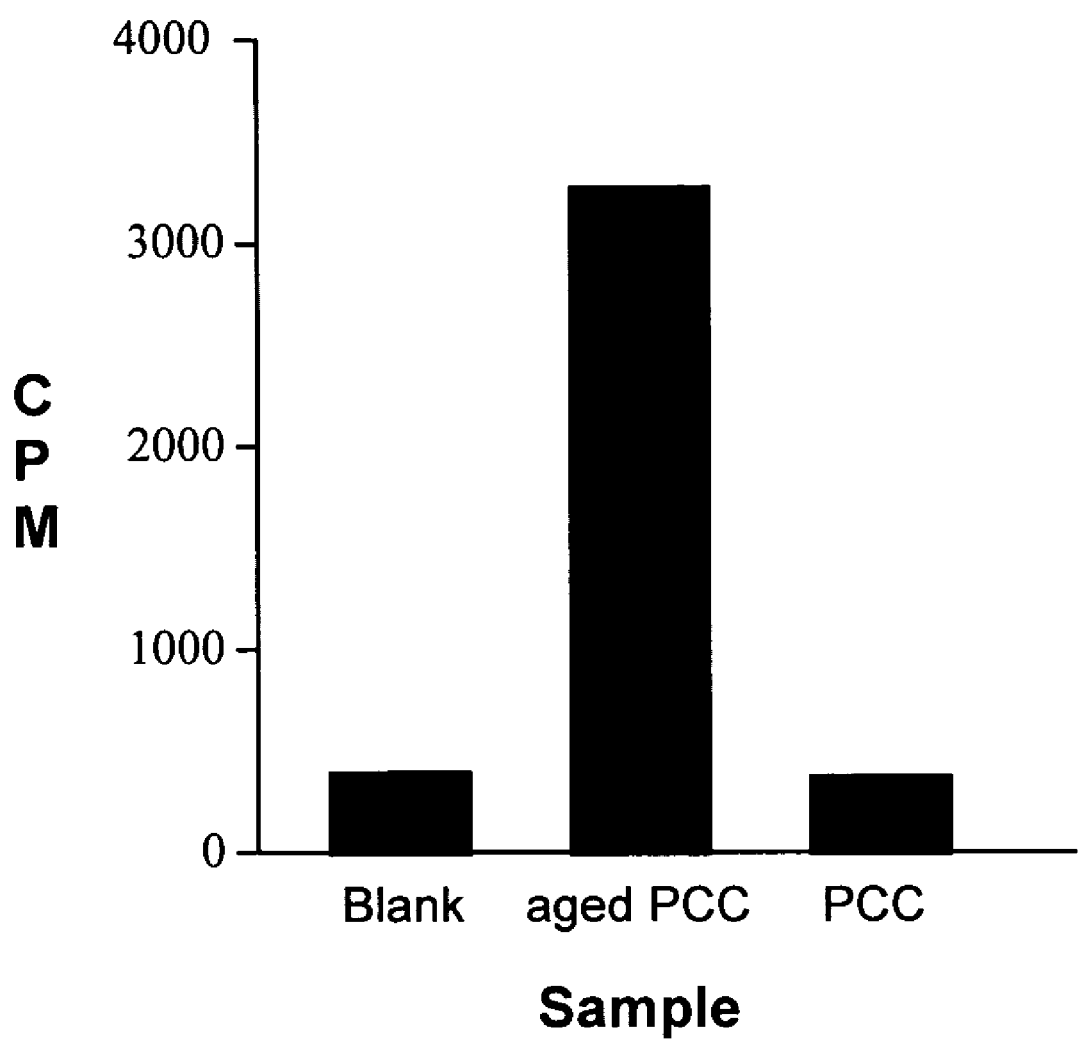
FIG. 1 shows aged proteins accumulate high levels of isoaspartyl residues.

The present inventors have previously shown that isoaspartyl modifications of "self" proteins (e.g., proteins recognized by a cell as it's own) can result in autoimmunity. The fundamentally important feature of these observations was that autoimmunity could be generated to isoaspartyl-modified self proteins, such as cytochrome c, while the identical unmodified protein would elicit no response from the immune system (Mamula, M. J. et al., J. Biol. Chem. 274: 22321-22327, 1999). In these studies, mice immunized with the murine cytochrome c peptide 90-104 showed no response by the B or T cell compartments. However, immunization with the isoaspartyl form of this peptide, where the linkage of Asp-93 to Leu-94 occurs through a β-carboxyl group, resulted in strong B and T cell autoimmune responses. Applications of this phenomenon to treatment of diseases, however, were not disclosed.

It has now been surprisingly discovered that specific cell surface proteins that are immunologically inert, such as tumor antigens, bacterial proteins, or viral proteins, may also be isoaspartyl-modified to elicit a strong immune response. As described in detail below, isoaspartyl modifications of these destructive, but immunologically inert proteins result in their being identified by the immune system as an invading body, and are targeted for elimination. The initiation of autoimmunity to these invading bodies can be an effective strategy in which to remove or degrade established solid and/or circulating tumor cells, or bacterial or viral pathogens.

Applications of this biological response are important in enhancing immune responses to many proteins, particularly those proteins such as tumor antigens and bacterial and viral proteins, which are identified by the cells to be "self" proteins, but are capable of harming or destroying the cell.

In accordance with the methods of the present invention, aspartic acid or asparigine residues in immunologically inert cell surface proteins can be post-translationally modified to isoaspartic acid resides. The isoaspartic acid residues confer autoimmunity to the cell surface proteins, and, by extension, to the cell itself, thus making them targets for the immune system. Thus, it is now possible to enhance the immune response of a patient by modifying these cell surface proteins such that the immune system of the patient specifically targets these pathogenic cells.

In accordance with one embodiment of the method of the present invention, tumor cells, or bacteria or viruses, may be isolated from the patient, and cultured ex vivo in the presence of compounds that that enhance isoaspartyl protein formation. In one embodiment, the cells are grown in the presence of adenosine dialdehyde (periodate-oxidized adenosine sold under the trade name AdOX). This compound is known to inhibit protein carboxymethyl transferase (PCMT), an intracellular enzyme that is responsible for repairing isoaspartyl modifications. The product of adenosine dialdehyde treatment of living cells is to inhibit the PCMT repair mechanism thereby allowing the accumulation of isoaspartyl-containing proteins (Johnson, B. A., et al. J. Biol. Chem. 268:6174-6181, 1993; Najbauer et al. Arch. Biochem. Biophys. 293:85-92, 1992; Najbauer et al. Anal. Biochem. 197:412-420, 1991).

In accordance with the method of the present invention, tumor cells may be extracted from the patient and incubated for 1-5 days at approximately 25-40° C. in the presence of 15-30 μM adenosine dialdehyde. Tumor cell extracts of adenosine dialdehyde-treated and untreated cells (both intracellular and membrane fractions) can be assayed for the levels of isoaspartyl modification by commercial assay (Promega, Inc.). Both living tumor cells and cellular extracts in complete Freund's adjuvant (CFA) can individually be used to transfer/immunize the patient. If a cellular extract is preferred, the treated cells can be lysed, and the modified protein isolated using procedures know in the art. After 12-21 days, CD8 T cells and serum antibodies can be assayed for tumor cell killing. In addition, the patient will be examined for the ability to resist subsequent tumor cell challenges.

This approach has the advantage to make use of individual tumor cell properties that may be characteristic to an individual patient, and bypasses the potential problems where individual major histocompatibility genes differ between individuals (i.e., specific tumor peptides may not bind comparably to all MHC surface proteins of cells of the immune system).

In accordance with another embodiment of the method of the present invention, peptides of tumor cell antigens or bacterial or viral proteins, containing isoaspartyl residues may be isolated or synthesized, and administered to a patient. The effect of administration of these modified peptides is the same as administration of whole cells or cellular extracts described above, and the result is an enhancement of immune response to the tumor antigens, or bacterial or viral proteins. Preferably, the naturally occurring peptide sequence contains an aspartic acid or asparigine residue that has been substituted with an isoaspartyl residue. In one embodiment, known tumor cell antigens whose amino acid sequence are known can be used. The most appropriate sequences for isoaspartyl modification include the sequences: Asn-Gly, Asn-Ser, Asp-Gly, and Asp-Ser. These sequences are advantageously selected because their conversion to isoaspartyl isoforms are known to occur spontaneously in nature. However, any Asp or Asn containing protein or peptide may undergo isoaspartyl modification.

In one embodiment, two peptides of 9 to 40 amino acids in length will be synthesized, more preferably, two peptides of 9 to 25 amino acids in length, and most preferably two peptides of 9 to 15 amino acids in length. One peptide contains the isoaspartyl modified residue and the other contains the aspartyl (normal) isoform amino acid. From 50 to 100 μg of individual peptides emulsified in complete Freund's adjuvant (CFA) may be used to subcutaneously immunize separate groups of patients. After 10 to 21 days, lymph node cells and serum antibodies will be removed and examined for anti-tumor immunity. MHC class I restricted tumor killing will be examined by conventional $^{51}$Cr release assays and antibody-complement mediated killing will be examined in vitro.

In particularly preferred embodiments, immunity to a human melanoma antigen, tyrosinase, may be elicited using the above procedure. A known melanoma antigen from the tyrosinase protein has been found to be a target of T lymphocytes (van der Bruggen, P. C., et al. Science 254:1643-1647, 1991; Brichard, V. A., et al., J. Exp. Med. 178:489-495, 1993; Cox, A. L., et al. Science 264:716-719, 1994; Skipper, J. C. A., et al. J. Exp. Med. 183:527-534, 1996). A naturally occurring 9 amino acid peptide, Tyr-Met-Asp-Gly-Thr-Met-Ser-Gln-Val (SEQ ID NO:1), binds the human HLA-A2.1 class protein and is a target of T lymphocyte responses (Skipper, J. C. A., et al. J. Exp. Med. 183:527-534, 1996). Based on the above information, patients are immunized with either isoaspartyl or aspartyl form of the tyrosinase peptide in CFA. After 12 days, CD8 T cells are removed and assayed for tumor cell killing of $^{51}$Cr-labeled melanoma cells.

Alternatively, patients may be immunized in longer term protocols and serum antibodies will be examined for the ability to kill $^{51}$Cr-labeled melanoma cells by antibody-complement mediated mechanisms. These studies will identify and quantitate the efficacy of isoaspartyl-bearing peptides versus normal aspartyl containing peptides in the generation of anti-tumor immunity.

In another embodiment of the method of the present invention, a proteinaceous tumor antigen, bacterial protein, or viral protein, or a fragment thereof, may be isolated and treated chemically to convert aspartic acid residues or asparigine residues to isoaspartic acid residues in vitro. These isoaspartic acid-containing proteins may be administered to the patient to elicit an enhanced immune response to the tumors, bacteria, and viruses that carry these proteins. Preferable methods of chemical treatment of the proteinaceous tumor antigen, bacterial protein, or viral protein include, but are not limited to, exposing the proteins to acidified methanol (McFadden et al., J. Biol. Chem. 261:11503-11511, 1996), or exposing the proteins to from 1-20% carbon dioxide ($CO_2$), and preferably approximately 5% carbon dioxide.

The present invention also encompasses vaccines that may be used to treat tumors, or pathogenic bacteria or viruses in patients. The vaccine of the present invention comprises a pharmaceutically acceptable carrier and a proteinaceous tumor antigen, a bacterial protein, a viral proteins, or a fragment thereof, where one of the aspartic acid residues or one of the asparigine residues has been replaced or modified to an isoaspartic acid residue. The vaccine of the present invention may be made using the above methods and combining the isoaspartyl-modified cells, proteins, protein extracts, or synthetic peptides with the pharmaceutically acceptable carrier.

Pharmaceutically acceptable carriers for the vaccine of the present invention can be either solid or liquid, and can broadly include electrolyte solutions, anal suppositories, topical creams, sublingual lozenges, water soluble jellies, enema solutions, inhalable aerosols, and the like. Solid form preparations can also include powders, tablets, pills, capsules, cachets, and dispersible granules. A solid carrier can be one or more substances which may also act as diluents, flavoring agents, binders, preservatives, tablet disintegrating agents, or an encapsulating material such as gelatin. If desired, the vaccine of the present invention can be sterilized and/or contain conventional pharmaceutical adjuvants, such as preservatives, stabilizing agents, wetting agents, emulsifying agents, buffers, or salts used for the adjustment of osmotic pressure. The pharmaceutical preparations may also contain other therapeutically active materials.

In powders, the carrier is preferably a finely divided or crushed solid which is in a mixture with the proteinaceous tumor antigen, bacterial protein, viral protein, or a fragment thereof. In tablets, proteinaceous tumor antigen, bacterial protein, viral protein, or a fragment thereof is mixed with a carrier having the necessary binding properties in suitable proportions and compacted in the shape and size desired. The powders and tablets preferably contain from 1% to about 20% of the proteinaceous tumor antigen, bacterial protein, viral protein, or a fragment thereof. Suitable carriers for crushable tablets include magnesium carbonate, magnesium stearate, talc, sugar, lactose, pectin, dextrin, starch, gelatin, tragacanth, methylcellulose, sodium carboxymethycellulose, low melting waxes, cocoa butter, and the like.

Liquid form preparations include solutions, suspensions, and emulsions, for example, water or water-propylene glycol, cetyl alcohol, or electrolyte or saline solutions. For parenteral injection, liquid preparations can be formulated in solution in aqueous polyethylene glycol solution. For intranasal administration, vaccine may be combined with an appropriate carrier such as an electrolyte (e.g., saline) solution.

The vaccine of the present invention can be prepared and administered in a wide variety of dosage forms. Thus, the composition of the present invention can be administered by injection, that is, intravenously, intramuscularly, intracutaneously, subcutaneously, subdermally, or intraperitoneally. Also, the vaccine of the present invention can be administered by inhalation, for example, intranasally, in either a liquid or solid aerosol. Additionally, the vaccine of the present invention can be administered transdermally (e.g., through a dermal "patch" or by direct topical application using a cream).

The vaccine preparation of the invention should include an amount of proteinaceous tumor antigen, a bacterial protein, a viral proteins, or a fragment thereof effective for treating the tumor or pathogenic bacteria or virus. The effective dosage will depend on the activity and toxicity of the particular tumor or pathogen to be eradicated, and is thus within the ordinary skill of the art to determine for any particular host mammal or other host organism. Suitable dosages may be, for example, in the range of about 0.5-15 mg per kg for a human being. Alternatively, the vaccine may be used to control proliferation of neoplastic cells or pathogenic organisms in vitro, or they may be used as antineoplastic or antipathogenic agents in nonhuman mammals.

The present invention also encompasses antibodies that may be used to treat tumors, or pathogenic bacteria or viruses in patients. The antibodies of the present invention are reactive with a protein or fragment thereof from a tumor antigen, a bacterial protein, or a viral protein that comprises an isoaspartic acid residue. Significantly, antibodies of the present invention that are generated to isoaspartyl forms of tumor antigens, or bacterial or viral proteins, are promiscuous in their ability to bind the normal aspartyl forms of the proteins. Thus, the antibodies not only bind to the isoasparyl forms of the tumor antigens, or bacterial or viral proteins, but to the aspartyl and aspariginyl forms as well. The antibodies may be made and isolated by conventional techniques, such as those described by Freifelder (Physical Biochemistry, Second Edition, 1982, W.H. Freeman & Co., pp. 323-352).

The methods, vaccines, and antibodies of the present invention are useful for enhancing immune response in any mammal, including humans, that possesses tumors, or pathogenic bacteria or viruses. The methods, vaccines, and antibodies of the present invention may also be used with any tumor antigen, pathogenic bacteria or virus. Examples of tumors that may be effectively treated with the methods of the present invention include solid tumor masses (e.g., carcinomas and sarcomas), including, but not limited to murine B16 melanoma, P815 murine mastocytoma, PTAS murine mammary carcinoma, colon rectal carcinoma, adenocarcinoma, glioblastoma multiform and astrosarcoma, cervial carcinoma, lung carcinomas, lymphomas (Hodgkin's and non-Hodgkin's), fibrosarcoma, myeloma, and the like. Other suitable tumors are well known to those of skill in the art.

Examples of tumor antigens that may be modified to include isoaspartyl residues include tyrosinase, MHC class I restricted and MHC class II restricted tumor antigens including melanoma differentiating antigens such as MART-1 (Melan-A), gp100 (pmel-17), tyrosinase, tyrosinase related protein-1 (TRP-1), tyrosinase related protein-2 (TRP-2), and melanocyte-stimulating hormone receptor; mutated antigens, such as beta-catenin, MUM-1, CDK-4, Caspase-8, and KIA0205; cancer testes antigens, such as MAGE-1, MAGE-2, MAGE-3, MAGE-12, BAGE, GAGE, and Ny-ESO-1; and shared antigens, such as alpha-Fetoprotein, telomerase catalytic protein, G-250, MUC-1, carcinoembryonic antigen (CEA), p53, and Her-2/neu. Particularly preferred tumor antigens for use in the methods of the present invention include those antigens that possess an aspartic acid or an asparigine residue, and more particularly those antigens that possess the sequences Asn-Gly, Asn-Ser, Asp-Gly, or Asp-Gly.

Any bacteria may be treated according to the methods of the present invention. Nonlimiting examples of bacteria that may be effectively treated with the methods of the present invention include *Bacillus*, such as *Bacillus anthracis*, *Mycobacterium*, *Streptococcus*, *Staphylococcus*, *Neisseria*, *Chlamydia*, *Haemophilus*, *Borrelia burgdorferi*, and the like. These bacteria contain surface proteins that may be effectively treated using the methods of the present invention. Examples of such bacterial proteins include bacterial porin proteins, such as PhoE, OmpF, or OmpC; porin-like proteins, such as LamB; O-antigens; lipoproteins; flagella proteins; bacterial adhesins that inhabit the bacterial cell membrane, and the like.

Any virus may be treated according to the methods of the present invention. Nonlimiting examples of viruses that may be effectively treated with the methods of the present invention include Hepatitis A, Hepatitus B, Hepatitus C, Rabies, HIV, Influenza, Measles, Rotavirus, Herpes simplex virus, and the like. These viruses contain surface proteins that may be effectively treated using the methods of the present invention. Examples of such viral proteins include HIV gp120, gp41, Hepatitis B surface antigens (HBsAg) and core antigen (HbcAg), and capsid proteins.

EXAMPLES

The following examples are intended to illustrate, but in no way limit the scope of the present invention. All parts and percentages are by weight and all temperatures are in degrees Celsius unless explicitly stated otherwise.

Animals

BIO.A, BIO.BR, and MRL lpr/lpr mice were purchased from the Jackson Laboratory, Bar Harbor, Me.

Quantitative Detection of Isoaspartyl-Modified Residues

Isoaspartyl residues were detected by the enzyme, protein isoaspartyl methyltransferase, according to the manufacturer's protocol (ISOQUANT™ Protein Deamidation Detection Kit, Promega Corp., Madison, Wis.). In brief, samples and control peptides are incubated 30 min. at 30 C in a reaction mixture containing protein isoaspartyl methyltransferase, [$^3$H]S-adenosyl-L-methionine, and cold S-adenyl-L-methionine. The reaction is stopped at pH 10 on ice and volatile [$^3$H]methanol is condensed in the reaction vessel. Fifty µl of sample is adsorbed to a sponge attached to the cap of a scintillation vial. The sample is incubated 60 min. at 40 C to volatize [$^3$H]methanol into the scintillation mixture and counted for counts/min. Positive controls include those provided in the ISOQUAN™ kit as well as synthetic peptides described above containing 1 isoaspartyl residue/peptide (1 µmol of [$^3$H]methanol/pmol of protein).

In some experiments, isoasparyl levels were examined in mitogen-activated B and T lymphocyte populations. In brief, freshly isolated splenic or lymph node B and T cells ($5\times10^5$/ml) were cultured with either lipopolysaccharide (10 µg/ml) for 48 h r with concanavalin A (10 µg/ml) for 24 h at 37 C. Cell pellets ($10^4$ cells) were collected from each culture, lysed by sonication in 100 µl of PBS/Tween, and assayed for isoaspartyl content as described above. Control cultures were incubated under identical conditions in the absence of lipopolysaccharide or concanavalin A.

T Cell Proliferation Assays

B10.A mice were immunized subcutaneously with 100 µg of either isoform of the murine snRNP D or cytochrome c peptide in PBS emulsified in complete Freund's adjuvant (Difco). After 10 days, the draining lymph nodes (popliteal, inguinal, and periaortic) were excised and single cell suspensions were prepared. Cells were cultured in triplicates ($5\times10^5$ cells/well) in 200 µl of Clicks medium (Irvine Scientific) supplemented with 5% fetal bovine serum, L-glutamine $5\times10^{-5}$ M 2-mercapotethanol, and antibiotics). Antigen stimulation was provided by adding the aspartyl or isoaspartyl isoforms of the snRNP D or cyto chrome c peptides, whole mouse cytochrome c (Sigma), or purified native murine snRNPs, as indicated. After 3 days, cultures were pulsed with 1 µCi of [$^3$H]thymidine, harvested 16 h later onto glass fiber filters, and counted in a BetaPlate liquid scintillation counter (LKB Wallac). Bar graphs represent cultures in which the deviation was less than 10% of the mean counts/min of triplicate cultures. Individual experiments utilized two to three mice immunized with each peptide. The data are representative of at least six individual proliferation experiments.

Autoantibody Analysis

Groups of four to six B10.A mice were immunized at day 0 with 50 µg of the indicated peptide emulsified in complete Freund's adjuvant and boosted with the same peptide in incomplete Freund's adjuvant at day 21. Mice were bled at day 28 and at weekly intervals thereafter.

Antibody binding to individual peptides was measured by ELISA and reported as optical density (405 nm). Polystyrene plates were pretreated with 0.2% glutaraldehyde 100 mM phosphate buffer at pH 5.0 for 3 h at room temperature. After washing with PBS, peptides were added at a concentration 5 µg/ml PBS (pH 8.0) for 2 h at room temperature. Plates were blocked with 1% bovine serum albumin in PBS before use. All subsequent wash steps used PBS with 0.5% Tween 20. Serum was diluted 1/200 in PBS/Tween with 0.1% bovine serum albumin and incubated in wells for 4 h at room temperature. In some experiments, serum dilutions were preincubated for 4 h at room temperature with selected peptides or proteins (as indicated in figures) in order to examine specific solution phase inhibition of antibody responses. After a first incubation of plates with primary antibody, plates were washed three times with PBS/Tween. Bound antibody was quantitated by sequential incubations with alkaline phosphate-conjugated goat anti-mouse IgG (Southern Biotechnology Associates) and p-nitrophenyl phosphate in diethanolamine buffer as chromogenic substrate. NMS indicates the use of preimmune mouse serum. Anti-double-stranded DNA binding was similarly examined by commercially available ELISA (Arlington Scientific, Inc., Arlington, Tex.) according to the manufacturer's instructions. All data points and percent inhibitions were calculated from the mean of triplicate wells in which individual standard deviation was less than 15% of the mean O.D. (405 nm) signal.

Class II Peptide Binding Assays

Cells—The B cell lymphoma CH-27 was used as a source I-$A^k$ and I-$E^k$ MHC class II molecules. The cell line was maintained in vitro by culture in RPMI 1640 medium supplemented with 2 mM L-glutamine, 50 µM 2-mercaptoethanol, 10% heat-inactivated fetal calf serum, 100 µg/ml streptomycin (Irvine Scientific, Santa Ana, Calif.), and 100 units/ml penicillin (Life Technologies, Inc., Grand Island, N.Y.). Large quantities of cells were grown in spinner cultures. Cells were lysed at a concentration of $10^k$ cells/ml in PBS containing 1% Nonidet P-40, 1 mM phenylmethylsulfonyl fluoride, 5 mM sodium orthovanadate, and 25 mM iodacetamide. The lysates were cleared of debris and nuclei by centrifugation at 10,000×g for 20 min.

Affinity Purification of Class II Molecules—Mouse class II molecules were purified as described previously (Gorga, J. C., et al., J. Biol. Chem. 262:16087-16094, 1987; Sette, A. et al., J. Immunol. 142:35-40, 1989) using the 10.3.6 monoclonal antibody (I-$A^k$-specific) and 14.4.4 (I-$E^{d-k}$-specific), coupled to Sepharose 4B beads. Lysates were filtered through 0.8- and 0.4-µm filters and then passed over the appropriate antibody columns, which were then washed with 15 column volumes of 0.5% Nonidet P=40, 0.1% SDS and 2 column volumes of PBS containing 0.4% n-octylglucoside. MHC class II was eluted with 0.05 M diethylamine in 0.15 M NaCl containing 0.4% n-octylglucoside (pH 11.5). A 1/20 volume of 1.0 M Tris, 1.5 M NaCl (pH 6.8) was added to the eluate to reduce the pH to ~7.5, and then concentrated by centrifugation in Centriprep 30 concentrators (Amicon, Beverly Mass.).

Class II Peptide-binding Assays—Purified mouse class molecules (5-500 nM) were incubated with 1-10 mM $^{125}$I-radiolabeled peptides for 48 h in PBS containing 5% dimethyl sulfoxide in the presence of a protease inhibitor mixture. Purified peptides were iodinated using chloramine-T method (Boos, S. et al., Science 235:1353-1358, 1987). Radiolabeled probes used were HEL p46-61 for I-$A^k$ and λ-repressor 12-26 for I-$E^k$. I-$A^k$ and I-$E^k$ assays were performed at pH 5.0 (Molberg, O., et al., Nature Med. 6:713-717, 1998).

Peptide inhibitors were typically tested at concentrations ranging from 120 µg/ml. The data was then plotted and the dose yielding 50% inhibition (IC$_{50}$) was measured. In appropriate stoichiometric conditions, the IC$_{50}$ of an unlabeled test peptide to the purified MHC is a reasonable approximation of the affinity of interaction (K$_d$). Peptides were tested in two to four completely independent experiments.

Class II peptide complexes were separated from free peptide by gel filtration on TSK2000 columns (TosoHaas 16215, Montgomeryville, Pa.) and the fraction of bound peptide calculated as described previously (Sette, A. et al., J. Immunol. 142:35-40, 1989). In preliminary experiments, each of the I-A and I-E preparations were titered in the presence of fixed amounts of radiolabeled peptides to determine the concentration of class II molecules necessary to bind 10-20% of the total radioactivity. All subsequent inhibition and direct binding assays were then performed using these class II concentrations.

Isoaspartyl Generation Acidic Methanol Treatment

In general, this procedure follows the protocol published by McFadden and Clarke (J. Biol. Chem. 261: 11503-11511, 1996). Briefly, selected protein is lyophilized if necessary. Approximately 200 µl of 0.1 N HCl in methanol (1 vol. conc. HCl: 120 final vol. methanol) is added to approximately 0.5 mg protein. The mixture is shielded from light and incubated for about 22 hours at room temperature (23° C.) to promote the esterification process. Following incubation, the mixture is diluted 5-6 fold with ddH$_2$O. The mixture is then frozen and lyophilized at a pressure of about 100 millitorr until dry. Following lyophilization, 200 µl sodium phosphate, pH 7.4, 25° C. is added, again shielded from light. The protein is then assayed for enzymatic methylation using protein deamidation analysis kit described above Isoaspartyl Generation by Adenosine Dialdehyde Treatment.

Briefly, selected cells, such as B16-F0 melanoma cells, are grown to confluency. The cells are then exposed to trypsin and counted. A T-25 flask is seeded with 2×10$^6$ cells, 30 µM Adenoside dialdehyde (Sigma, Adenosine, periodate oxidized), and the cells are grown at 37° C. for about 2 days. The cells are next harvested using trypsin, washed, and counted. The cells are isolated by centrifugation, and the supernatant is removed. The cells are resuspended in approximately 100 µL IPP buffer (10 mM Tris, 500 mM NaCl, 0.1% NP-40)+1 mM phenylmethylsulfonyl fluoride. The cells are then sonicated (3×30 sec, with 30 sec on ice in between sonications), and subjected to centrifugation at 14,000 rpm for 10 min at 40 C. The supernatants are collected and saved, and the pellet is resuspended in IPP buffer. Protein concentration is determined in both the supernatant and the pellet. Isoaspartyl generation is determined by ISOQUANT assay described above.

Example 1

Aged Proteins Show High Levels of Isoaspartyl Residues

A model protein, pigeon cytochrome c (PCC) and crude tumor cell lysates in PBS were incubated at 37° C. for 21 days and exposed to 5% carbon dioxide. Following treatment, the protein was assayed for the presence of isoaspartyl modifications in comparison with untreated proteins as described above. As shown in FIG. 1, aged proteins possess from two to four times the molarity of isoaspartyl modifications as compared to control proteins.

Example 2

Figure 2:
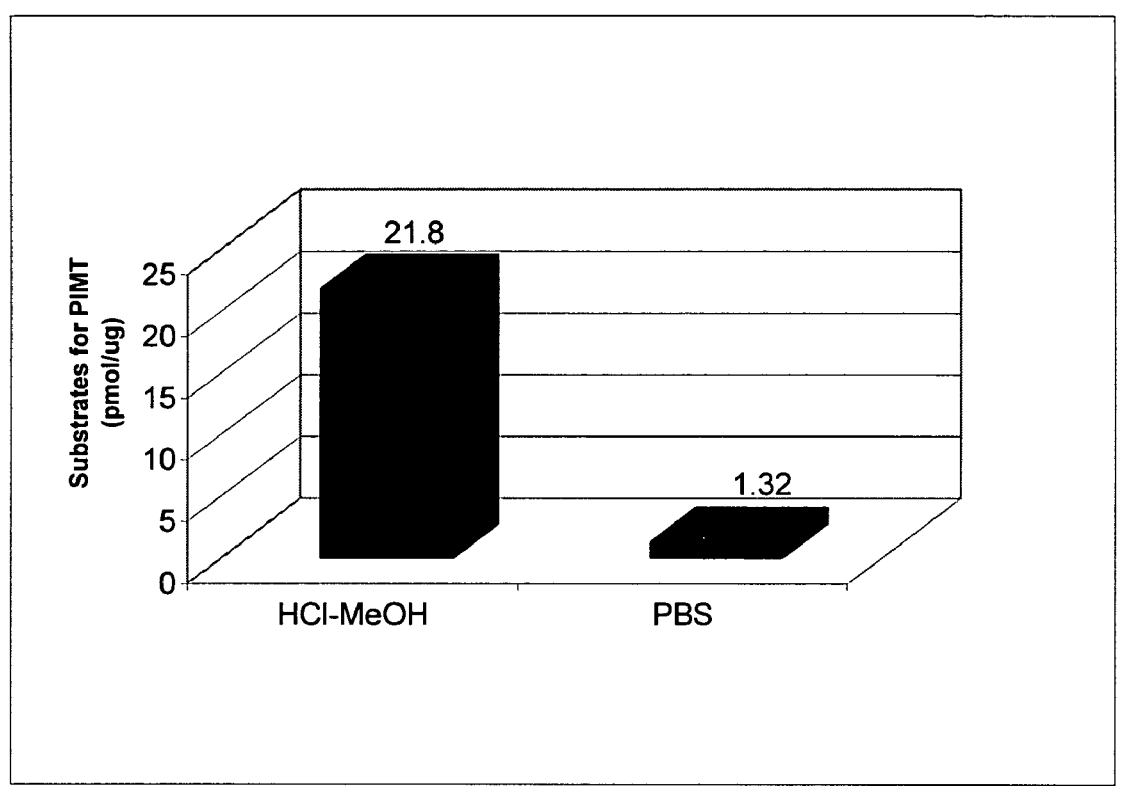
FIG. 2 shows that acid-methanol of B16 tumor cell lysates enhances the level of isoaspartyl modification twenty fold in comparison to untreated tumor cell lysates.

Acid-Methanol Treatment of B16 Tumor Cell Lysates Enhances the Level of Isoaspartyl Modification B16 tumor cells were lysed in phosphate buffered saline (PBS) and subjected to HCl-methanol treatment or untreated (in PBS) as described above. Five µg of protein was then assayed for the presence of isoaspartyl modification. As shown in FIG. 2, acid-methanol raised the isoaspartyl content of tumor protein nearly 20 fold as compared to untreated tumor lysate protein.

Example 3

Figure 3:
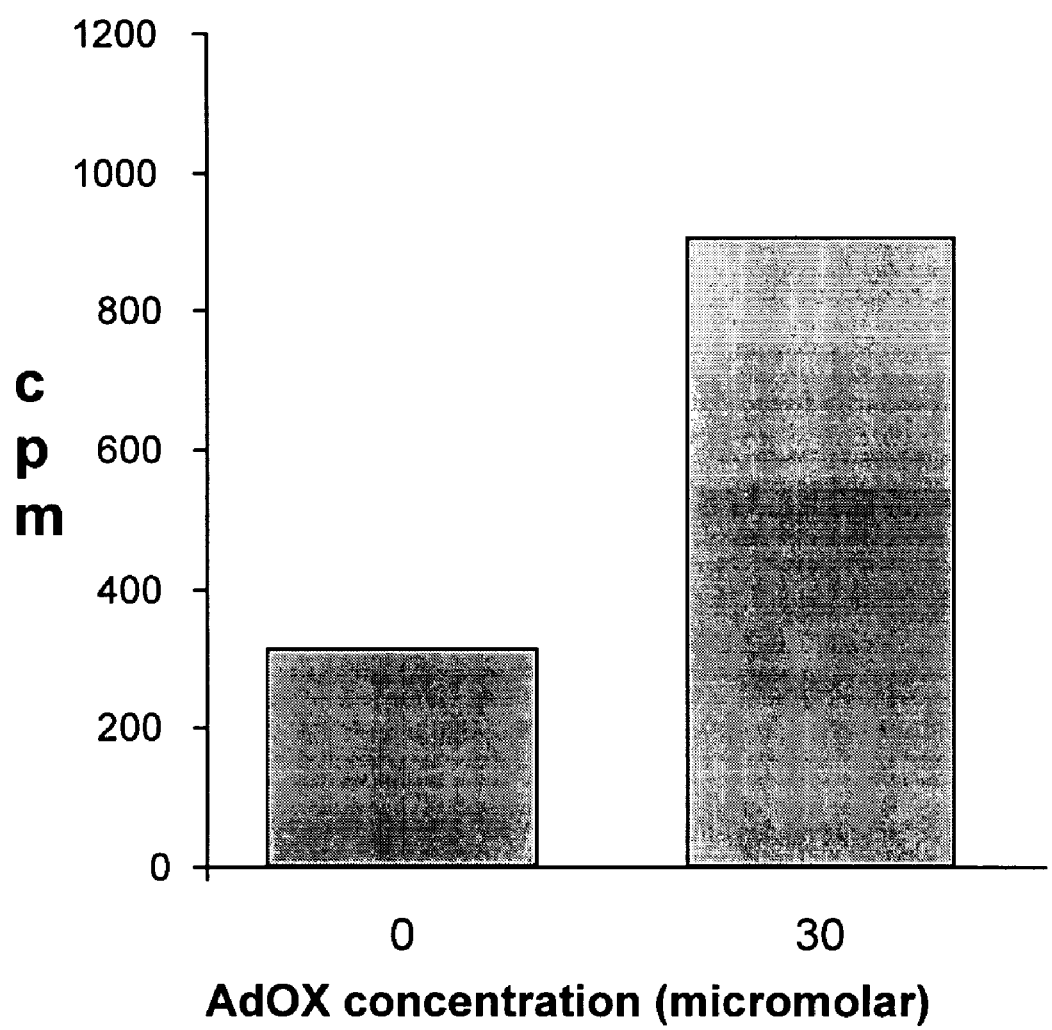
FIG. 3 shows that adenosine dialdehyde treatment of living B16 melanoma cells enhances isoaspartyl content in tumor proteins.

Adenosine Dialdehyde Treatment of Living B16 Melanoma Cells Enhances Isoaspartyl Content in Tumor Proteins In cell culture, B16 cells were incubated with 30 µM adenosine dialdehyde for 48 h as described above. Cells were then harvested and lysed in PBS. Isoaspartyl content was determined as described above. As shown in FIG. 3, isoaspartyl content was enhanced from two to five fold compared to untreated B16 cells.

Example 4

Figure 4:
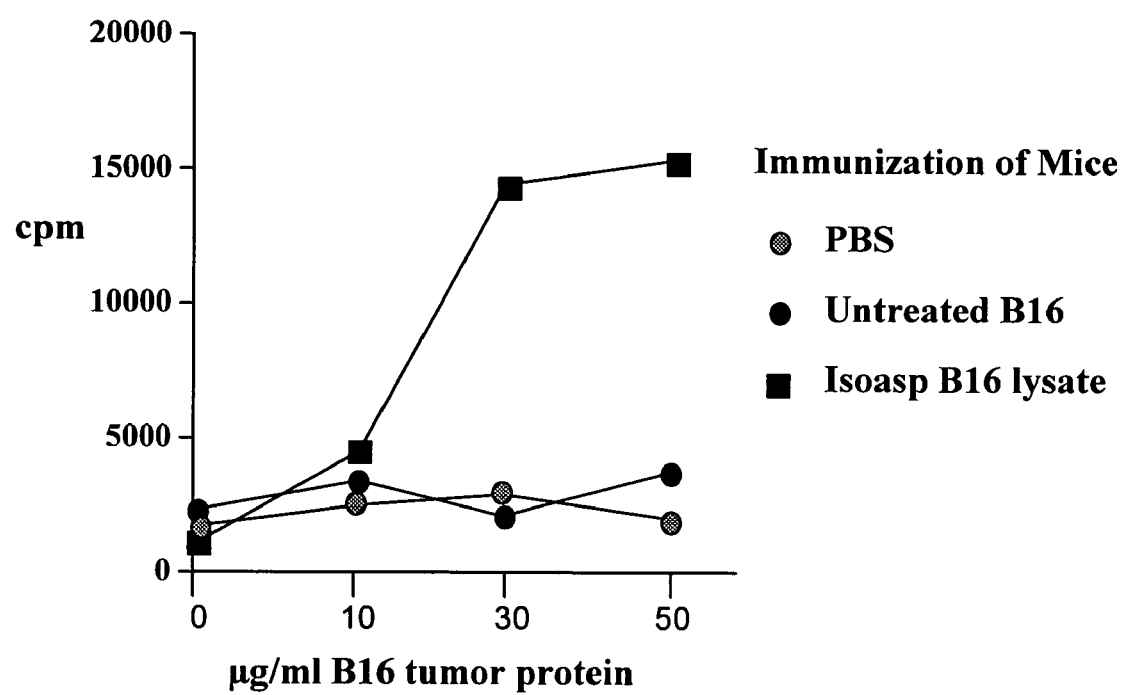
FIG. 4 shows that immunization of C57/B1/6 mice with acid-methanol treated tumor cell lysates elicits CD4 T cell immune responses.

Immunization of C57/B1/6 Mice with Acid-Methanol Treated Tumor Cell Lysates Elicit CD4 T Cell Immune Responses Mice were immunized with 100 µg of B16 tumor cell lysate in complete Freund's adjuvant (CFA). Control mice were immunized with unmodified tumor lysate/CFA adjuvant. After 14 days, lymph node T cells were stimulated with tumor cell lysate and pulsed with $^3$H-thymidine as a measure of T cell proliferation. As shown in FIG. 4, modified tumor lysate immune mice exhibited approximately 6 fold enhanced T cell stimulation as compared to T cells from mice immunized with unmodified tumor antigen proteins.

Example 5

Figure 5:
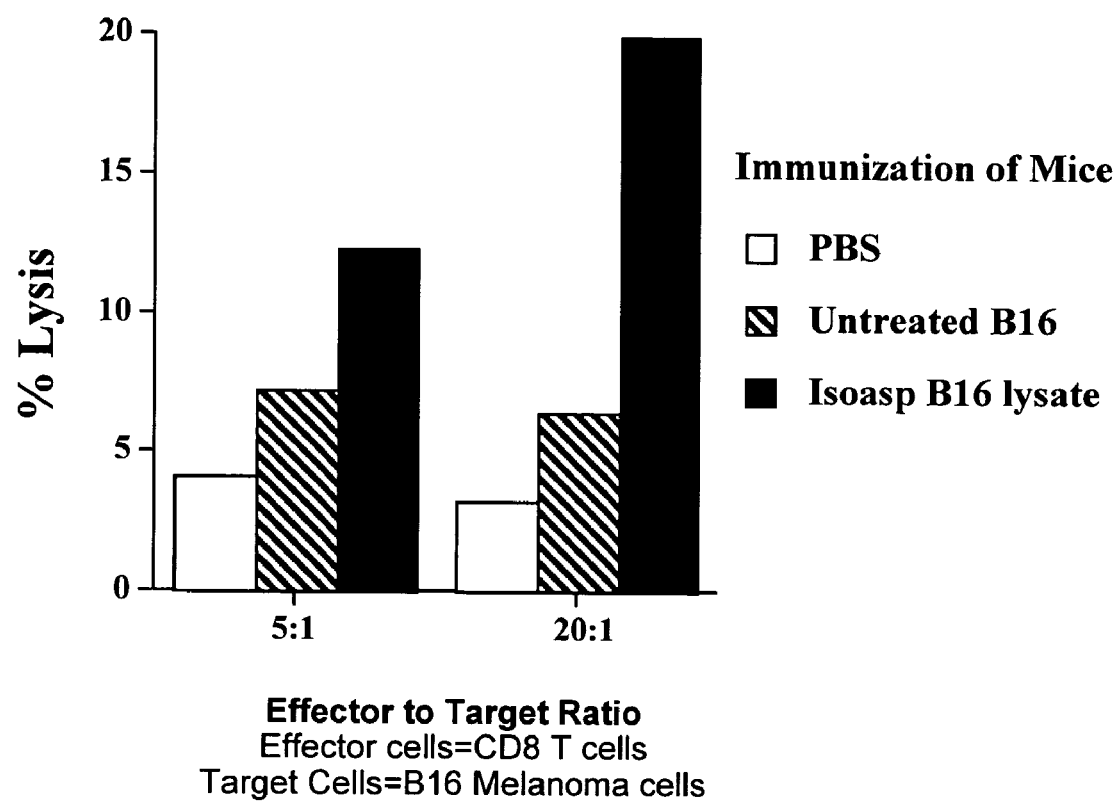
FIG. 5 shows killer CD8 T cells are elicited in mice immunized with isoaspartyl modified melanoma cell lysates.

Killer CD8 T Cells are Elicited in Mice Immunized with Isoaspartyl Modified Melanoma Cell Lysates Mice were immunized with either isoaspartyl modified tumor cell lysate or unmodified tumor cell lysates as prepared above. After 14 days, purified CD8 T cells were purified from mice and incubated for 7 days with irradiated B16 tumor cells and interleukin 2. After 7 days, T cells were re-purified and incubated with labeled B16 melanoma cell targets at 20:1 (effector T cell:tumor cell ratio). Percent lysis was measured by the release of intracellular label as compared to control B16 cell cultures. As shown in FIG. 5, while control treated animals exhibited less than 5% killing of target B16 cells, CD8 T cells from isoaspartyl immunized mice showed approximately 20-25% tumor cell killing in this procedure.

Example 6

Utility and Efficacy of Isoaspartyl Modified Tumor Peptides for the Treatment of Melanoma in a Murine Model B16F10 melanoma is a transplantable murine tumor cell widely studied in models of human melanoma. In brief, the FIGS. 6-12 illustrate that immunization with isoaspartyl modified melanoma tumor peptides elicit anti-tumor T cell and anti-tumor antibody responses. The T cells are specific for melanoma tumor peptides and respond to both isoaspartyl and aspartyl forms of the peptide. T cells elicited by isoaspartyl peptide immunization effectively kill tumor cells both in vitro and in vivo. Finally, isoaspartyl peptide immune mice are resistant to challenge with B16 melanoma cells, survive longer and show an infiltration of tumor tissues with CD8 T cells. In contrast, immunization with the aspartyl form of melanoma fails to elicit effective CD8 T cell or antibody responses and does not protect mice from challenge with melanoma tumor cells.

Figure 6:
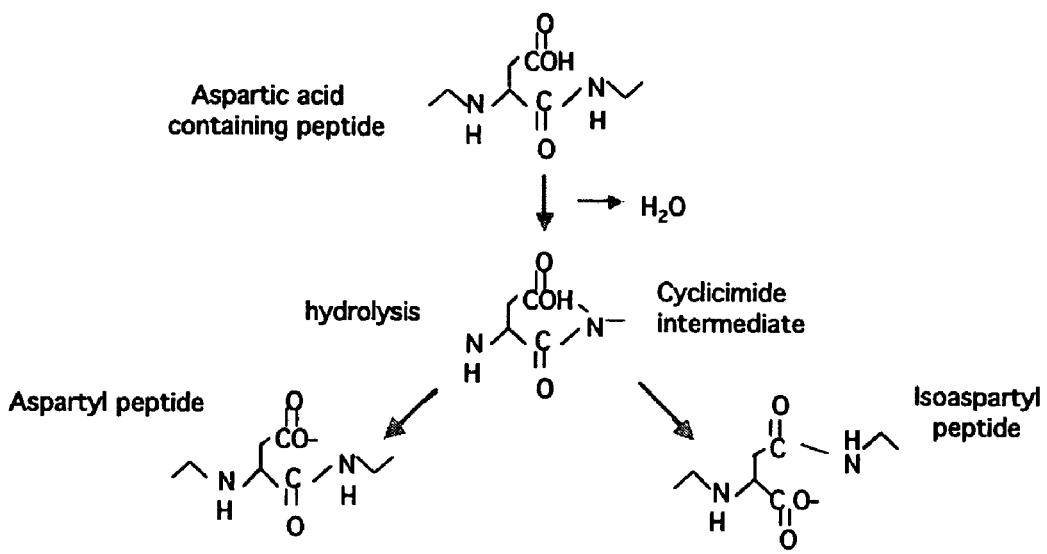
FIG. 6 shows the structural biochemistry of isoaspartyl formation and the amino acid sequence of melanoma TRP-2 synthetic peptides.

FIG. 6 illustrates the structural biochemistry of isoaspartyl formation and the amino acid sequence of melanoma TRP-2 synthetic peptides. TRP-2 protein is a melanoma tumor protein found on both human melanoma cells and on B16F10 murine melanoma cells. For this approach, TRP-2 peptide (sequence 181-188) was synthesized separately with an isoaspartyl amino acid modification at residue 183 (SEQ ID NO:3) or, conversely, an aspartic acid residue (SEQ ID NO:2). Peptides were used in HPLC purified form for immunizations.

Figure 7:
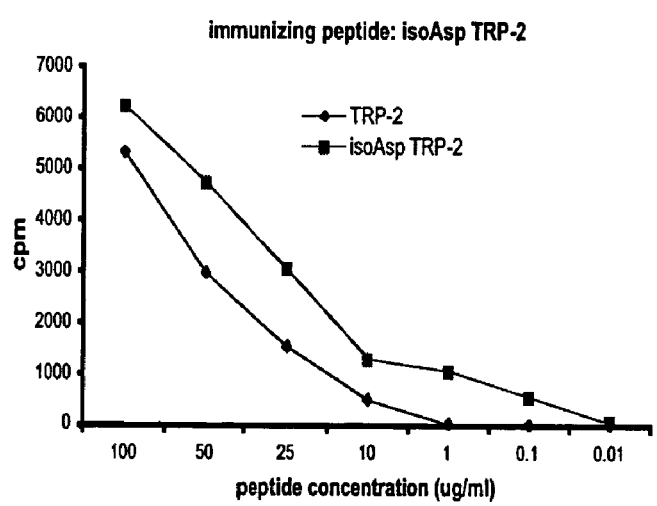
FIG. 7 shows that immunization with isoaspartyl TRP-2 peptide elicits CD8 T cells that proliferate in response to stimulation with isoaspartyl or aspartyl TRP-2 peptide.

FIG. 7 illustrates that immunization with isoaspartyl TRP-2 peptide elicits CD8 T cells that proliferate in response to stimulation with isoaspartyl or aspartyl TRP-2 peptide. For these studies, C57B1/6 mice are immunized subcutaneously with 50 µg of either isoaspartyl TRP-2 peptide or aspartyl TRP-2 peptide emulsified in complete Freund's adjuvant (CFA). After 7 days, lymph node cells are collected and CD8 T cells are purified by magnetic bead depletion of CD4+, B220+, CD11c+ cells. CD8 T cells ($1 \times 10^5$) are incubated for 3 days in tissue culture (37° C., 5% $CO_2$) with irradiated splenic antigen presenting cells (APCs; $5 \times 10^5$ cells) pulsed with isoaspartyl TRP-2 or aspartyl TRP-2 in the concentrations as indicated. As shown in FIG. 7, immunization with isoaspartyl TRP-2 peptide elicits cross reactive T cells that respond to stimulation with either isoaspartyl or aspartyl TRP-2 peptide. In contrast, immunization with aspartyl TRP-2 fails to elicit any detectable T cell responses (data not shown).

Figure 8:
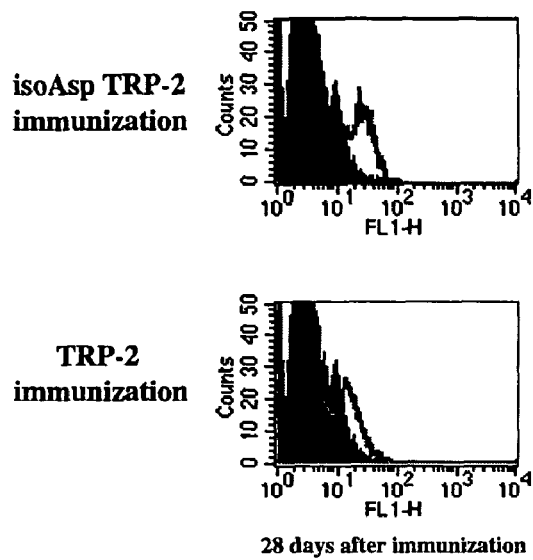
FIG. 8 shows that immunization with isoaspartyl TRP-2 elicits anti-tumor antibody responses.

FIG. 8 illustrates that immunization with isoaspartyl TRP-2 elicits anti-tumor antibody responses. Mice were immunized subcutaneously with 50 µg of isoaspartyl or aspartyl TRP-2 peptide, as indicated. Mice were bled at day 28 post immunization. Serum (1/100 dilutions in phosphate buffered saline (PBS)) was incubated with B16F10 melanoma cells ($5 \times 10^5$ cells) and analyzed by flow cytometry after the detection of bound antibody with anti-mouse IgG-FITC. As indicated by the discreet shift in the profile of the upper panel of FIG. 8, antibodies from isoaspartyl TRP-2 immune animals effectively bind B16F10 cells. In contrast, little or no anti-tumor antibodies are detected from animals immunized with aspartyl TRP-2.

Figure 9:
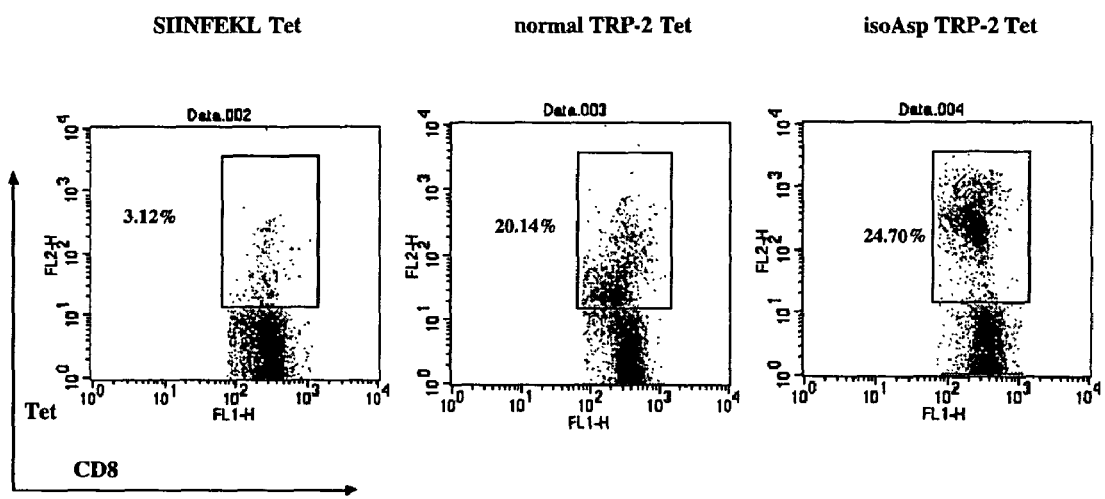
FIG. 9 shows that CD8 T cells specific for the TRP-2 peptide are elicited by immunization with isoaspartyl TRP-2 peptide.

FIG. 9 illustrates that CD8 T cells specific for the TRP-2 peptide are elicited by immunization with isoaspartyl TRP-2 peptide. Mice were immunized subcutaneously with 50 µg of isoaspartyl TRP-2 emulsified in CFA. At day 14 after immunization, lymph node cells were removed and single cell suspensions ($4 \times 10^6$ cells/ml) were incubated in culture with isoaspartyl TRP-2 peptide (10 µg/ml) for 5 days (37° C., 5% $CO_2$). Living cells were purified by Ficoll-hypaque and incubated with anti-CD8-FITC antibody (Promega Inc.) and MHC class I (H-2 Kb) tetramers linked to PE, as indicated. Tetramer staining was performed with a control, non-specific peptide (SIINFEKL) (SEQ ID NO:4) and with aspartyl and isoaspartyl TRP-2 peptide tetramers, as indicated. Expansion of lymph node cells in 5 day cultures profoundly stimulated the growth of CD8 T cells that were bound by aspartyl and isoaspartyl TRP-2 tetramers. In contrast, parallel studies performed in aspartyl TRP-2 immunized animals failed to stimulate TRP-2 specific CD8 T cells (data not shown).

Figure 10:
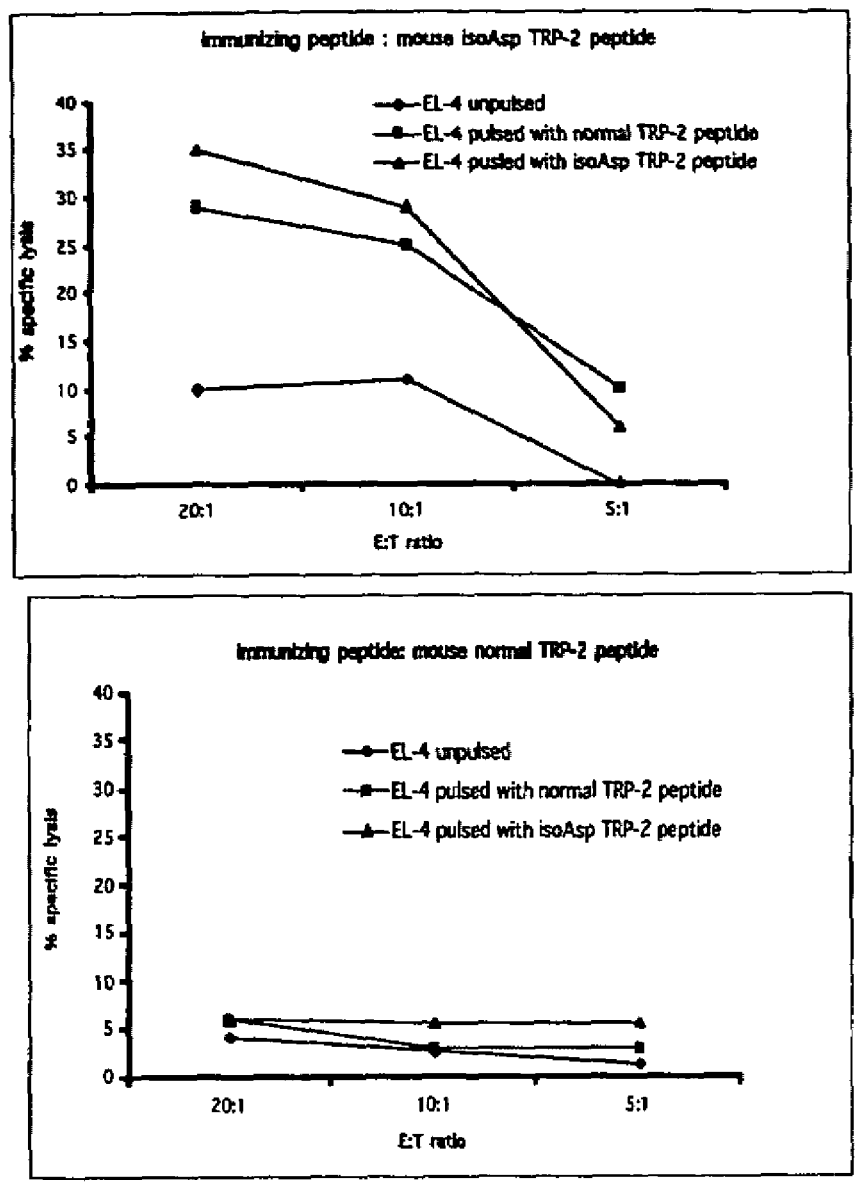
FIG. 10 shows that immunization with isoaspartyl TRP-2 peptide elicits CD8 T cells that kill tumor peptide bearing target cells.

FIG. 10 illustrates that immunization with isoaspartyl TRP-2 peptide elicits CD8 T cells that kill tumor peptide bearing target cells. Mice were immunized with isoaspartyl or aspartyl TRP-2 (50 µg in CFA), by subcutaneous route. Lymph node cells were expanded in vitro for 5 days with isoaspartyl TRP-2 as described above. After 5 days, purified effector CD8 T cells were mixed with EL-4 target cells pulsed with isoaspartyl TRP-2, aspartyl TRP-2, or unpulsed EL-4 cells, as indicated. Averages of triplicate cultures are reported for effector to target ratios of 5:1, 10:1, and 20:1. Cytotoxicity was performed by commercial non-radioactive methods (Ctyotox 96, Promega, Inc.) according to the manufacturer's instructions. As indicated in the upper panel of FIG. 10, mice immunized with isoaspartyl TR-2 peptide kill up to 35% of TRP-2 pulsed target cells. In contrast, aspartyl TRP-2 immune animals fail to elicit cytotoxic T cell responses in this assay (lower panel of FIG. 10).

Collectively, these studies suggest that isoaspartyl modification of TRP-2 p181-188 elicits anti-tumor T cell responses that are cross-reactive for both the isoaspartyl and aspartyl form of TRP-2. In a manner similar to that found in autoimmunity, it is believed that epitope spreading occurs to other sites on the TRP-2 protein and, indeed, to other melanoma proteins that would further enhance anti-tumor immunity in this approach (Mamula, M. J., et al., Immunol. Rev. 164:231-239 (1998); Shlomchik, M. J., et al., Nature Rev. Immunol. 1: 147-154, (2001)).

As illustrated in Table I below, immunization with isoaspartyl TRP-2 also elicits immunity that lyses tumor peptide pulsed target cells in vivo models. In this approach, groups of 6 mice were immunized with isoaspartyl or aspartyl TRP-2 (50 µg in CFA), by subcutaneous route. At day 21 mice were examined for their ability to kill tumor peptide pulsed target cells (in vivo CTL assays) modified by the protocol of Coles, et al. (J. Immunol. 168:834-838 (2002)). In brief, two populations of syngeneic target spleen cells are labeled with low or high concentrations of CFSE (0.5 µM or 5.0 µM CFSE, respectively). Spleen cells labeled with 5.0 µM CFSE are pulsed with isoaspartyl or aspartyl TRP-2 peptide (1 µg/ml) as the in vivo target cell population. Both high CFSE labeled/TRP-2 peptide pulsed and low CFSE labeled/unpulsed spleen cells ($1 \times 10^7$ cells for each population) are transferred by intravenous route into immunized mice as described above. Mice were sacrificed at 16 hours and in vivo lysis of peptide pulsed targets is defined by flow cytometry technology as:

Ratio=% CFSE low/% CFSE high

% Specific Killing=[1−(ratio in control immunized/ratio in immunized)×100].

TABLE I

In Vivo Killing of Tumor Peptide Pulsed Target Cells

| Immunization | Target Cells Transferred | % Specific Killing |
|---|---|---|
| Aspartyl TRP-2 | Asp TRP-2 pulsed | 5 |
| Aspartyl TRP-2 | Isoasp TRP-2 pulsed | 22 |
| Isoaspartyl TRP-2 | Asp TRP-2 pulsed | 56 |
| Isoaspartyl TRP-2 | Isoasp TRP-2 pulsed | 60 |

Figure 11:
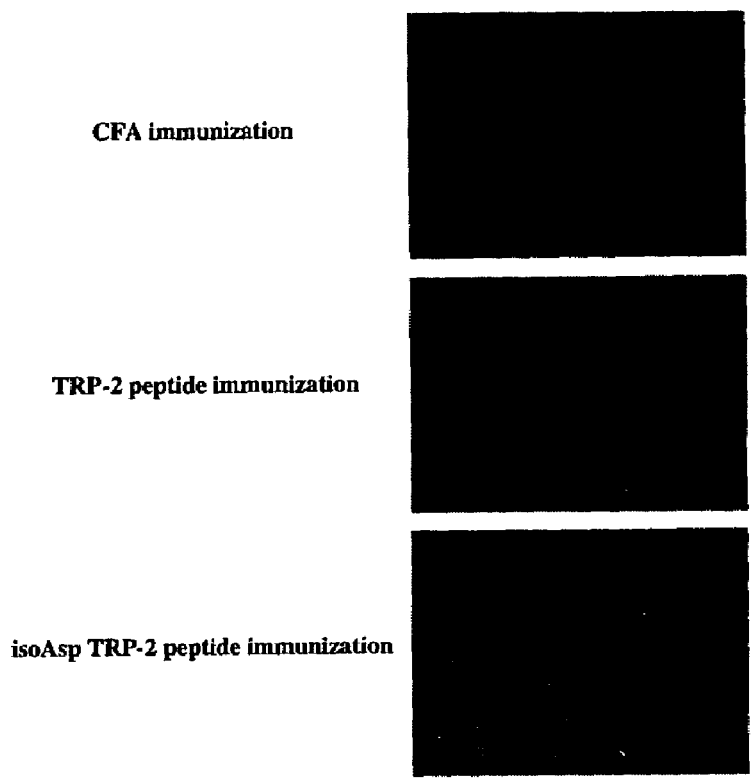
FIG. 11 shows an influx of CD8 T cells into melanoma tumor tissues of mice immunized with isoaspartyl TRP-2 immunized mice.

FIG. 11 illustrates an influx of CD8 T cells into melanoma tumor tissues of mice immunized with isoaspartyl TRP-2 immunized mice. In contrast, CFA control immune or aspartyl TRP-2 immune mice do not have an influx of CD8 T cells into tumor tissues. For these studies, mice were immunized with isoaspartyl or aspartyl TRP-2 (50 µg in CFA), by subcutaneous route. At day 21, mice were challenged with 0.5× $10^6$ B16F10 melanoma cells by subcutaneous route. At day 14 after tumor cell challenge, tumor masses were removed and stain for CD8 T cells by conventional immunohistochemistry. A significant influx of CD8 T cells are observed in tumor masses from isoaspartyl TRP-2 immune mice (red marked cells, lower panel of FIG. 11) while CFA control immune or aspartyl TRP-2 immune mice fail to show CD8 T cells in the tumor masses.

Figure 12:
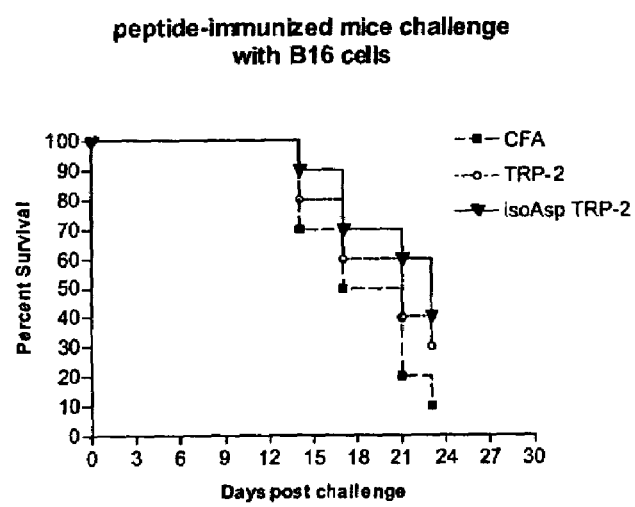
FIG. 12 shows enhanced survival in isoaspartyl TRP-2 immune mice challenged with B16F10 tumor cells.

FIG. 12 shows enhanced survival in isoaspartyl TRP-2 immune mice challenged with B16F10 tumor cells. For these studies, groups of 10 mice were immunized with isoaspartyl or aspartyl TRP-2 (50 µg in CFA), by subcutaneous route as described above. Mice were challenged subcutaneously at day 21 with $0.5 \times 10^6$ cells. Survival was assessed every 3 days. As illustrated in FIG. 12, isoaspartyl TRP-2 immune mice show greater survival as compared to mice immunized with aspartyl TRP-2 or CFA control immunizations.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entireties.

What is claimed is:

1. A method of enhancing the humoral immune response of a patient relative to the normal humoral immune response, comprising the steps of:
    growing cells containing a tumor antigen, a bacterial protein, or a viral protein under conditions wherein an aspartic acid residue or an asparigine residue in said tumor antigen, said bacterial protein, or said viral protein is converted to an isoaspartic acid residue to produce an isoaspartic acid-containing tumor antigen, an isoaspartic acid-containing bacterial protein, or an isoaspartic acid-containing viral protein, said conditions comprising exposing said cells to 15-30 μM adenosine dialdehyde at approximately 25-40° C. for 1-5 days;
    optionally isolating said isoaspartic acid-containing tumor antigen, an isoaspartic acid-containing bacterial protein, or an isoaspartic acid-containing viral protein; and
    administering said cells or said isolated isoaspartic acid-containing tumor antigen, an isoaspartic acid-containing bacterial protein, or an isoaspartic acid-containing viral protein to said patient to enhance the humoral immune response of said patient.

2. The method of claim 1, wherein said growing step comprises exposing said cells containing said tumor antigen, said bacterial protein, or said viral protein to adenosine dialdehyde.

3. The method of claim 1, wherein said cells are tumor cells selected from the group consisting of murine B16 melanoma, P815 murine mastocytoma, PTAS murine mammary carcinoma, colon rectal carcinoma, adenocarcinoma, glioblastoma multiform and astrosarcoma, cervial carcinoma, lung carcinomas, lymphomas, fibrosarcoma, and myeloma.

4. The method of claim 1, wherein said tumor antigen is selected from the group consisting of MART-1 (Melan-A), gp100 (pmel-17), tyrosinase, tyrosinase related protein-1 (TRP-1), tyrosinase related protein-2 (TRP-2), melanocyte-stimulating hormone receptor, beta-catenin, MUM-1, CDK-4, Caspase-8, KIA0205, MAGE-1, MAGE-2, MAGE-3, MAGE-12, BAGE, GAGE, Ny-ESO-1, alpha-Fetoprotein, telomerase catalytic protein, G-250, MUC-1, carcinoembryonic antigen (CEA), p53, and Her-2/neu.

5. The method of claim 1, wherein said aspartic acid residue or asparigine residue forms part of an amino acid sequence selected from the group consisting of Asn-Gly, Asn-Ser, Asp-Gly, and Asp-Ser.

6. A method of enhancing the humoral immune response of a patient relative to the normal humoral immune response, comprising the steps of:
providing a tumor antigen, a bacterial protein, or a viral protein, or a fragment thereof, wherein each of said tumor antigen, a bacterial protein, or a viral protein, or a fragment thereof comprises an aspartic acid residue or an asparigine residue;
treating said tumor antigen, a bacterial protein, or a viral protein, or a fragment thereof to convert said aspartic acid residue or said asparigine residue to an isoaspartic acid residue to produce an isoaspartic acid-containing tumor antigen, an isoaspartic acid-containing bacterial protein, an isoaspartic acid-containing viral protein, or isoaspartic acid-containing fragment thereof;
assaying for levels of isoaspartyl modification in the treated tumor antigen, bacterial protein, viral protein, or fragment thereof;
administering the isoaspartic acid-containing tumor antigen, isoaspartic acid-containing bacterial protein, isoaspartic acid-containing viral protein, or isoaspartic acid-containing fragment thereof to said patient to elicit said enhanced humoral immune response.

7. The method of claim 6, wherein said treating step comprises exposing said tumor antigen, said bacterial protein, or said viral protein, or said fragment thereof, to acidic methanol.

8. The method of claim 6, wherein said treating step comprises exposing said tumor antigen, said bacterial protein, or said viral protein, or said fragment thereof, to from 1-20% carbon dioxide.

9. The method of claim 6, wherein said tumor antigen is selected from the group consisting of MART-1 (Melan-A), gp100 (pmel-17), tyrosinase, tyrosinase related protein-1 (TRP-1), tyrosinase related protein-2 (TRP-2), melanocyte-stimulating hormone receptor, beta-catenin, MUM-1, CDK-4, Caspase-8, KIA0205, MAGE-1, MAGE-2, MAGE-3, MAGE-12, BAGE, GAGE, Ny-ESO-1, alpha-Fetoprotein, telomerase catalytic protein, G-250, MUC-1, carcinoembryonic antigen (CEA), p53, and Her-2/neu.

10. The method of claim 6, wherein said aspartic acid residue or asparigine residue forms part of an amino acid sequence selected from the group consisting of Asn-Gly, Asn-Ser, Asp-Gly, and Asp-Ser.

\* \* \* \* \*